(12) United States Patent
Litz et al.

(10) Patent No.: US 8,283,498 B2
(45) Date of Patent: Oct. 9, 2012

(54) OXIDATIVE DESULFURIZATION USING A TITANIUM(IV) CATALYST AND ORGANOHYDROPEROXIDES

(75) Inventors: Kyle E. Litz, Ballston Spa, NY (US); Jennifer L. Vreeland, Troy, NY (US)

(73) Assignee: Auterra, Inc., Malta, NY (US)

( * ) Notice: Subject to any disclaimer, the term of this patent is extended or adjusted under 35 U.S.C. 154(b) by 0 days.

(21) Appl. No.: 13/185,552

(22) Filed: Jul. 19, 2011

(65) Prior Publication Data

US 2012/0022272 A1 Jan. 26, 2012

Related U.S. Application Data

(60) Provisional application No. 61/365,842, filed on Jul. 20, 2010.

(51) Int. Cl.
*C07C 315/02* (2006.01)
(52) U.S. Cl. ......................................... 568/27
(58) Field of Classification Search ............... 568/27
See application file for complete search history.

(56) References Cited

U.S. PATENT DOCUMENTS

| 3,873,587 A | 3/1975 | Rosenthal et al. |
| 2006/0154814 A1 | 7/2006 | Zanibelli et al. |
| 2011/0011771 A1 | 1/2011 | Litz et al. |

OTHER PUBLICATIONS

International Search Report and Written Opinion mailed Dec. 6, 2011; PCT/US11/44439; Int'l File Date: Jul. 19, 2011; 7 pages.
Kholdeeva, Oxana A.; Titanium-monosubstituted polyoxometalates: relation between homogeneous and heterogeneous Ti-single-site-based catalysis; Topics in Catalysis, vol. 40, Nos. 1-4, Nov. 2006.

*Primary Examiner* — Taofiq A Solola
(74) *Attorney, Agent, or Firm* — Schmeiser, Olsen & Watts, LLP

(57) ABSTRACT

Oxidative desulfurization (ODS) is an attractive alternative to hydrodesulfurization (HDS) technology due to its lower energy requirement for the removal of refractory sulfur species, such as dibenzothiophene (DBT), from heavier petroleum streams. Diesel containing DBT may be oxidized using a heterogeneous titanium(IV) catalyst and organohydroperoxide oxidant, such as tert-butyl hydroperoxide (TBHP), cumyl hydroperoxide (CHP) and/or ethylbenzene hydroperoxide (EBHP), which proves effective for the selective oxidation and removal of refractory sulfur compounds from diesel fuel.

18 Claims, 8 Drawing Sheets

R = C₆H₅C(CH₃)₂, C₆H₅CH(CH₃), C(CH₃)₃
R' = H, CH₃

US 8,283,498 B2

OXIDATIVE DESULFURIZATION USING A TITANIUM(IV) CATALYST AND ORGANOHYDROPEROXIDES

CROSS REFERENCE TO RELATED APPLICATIONS

This application is a non-provisional patent application of the earlier provisional patent application entitled "Oxidative Desulfurization Using a Titanium(IV) Catalyst and Organic Hydroperoxides," Ser. No. 61/365,842, filed Jul. 20, 2010 now pending, the disclosures of which are hereby incorporated herein by reference.

BACKGROUND OF THE DISCLOSURE

In 2006, as part of the Clean Air Act, the Environmental Protection Agency (EPA) passed legislation to limit the sulfur content of roadway diesel fuels to ≦15 ppm by 2010. This regulation was developed to diminish the negative impact of $SO_x$ emissions on the environment. $SO_x$ is responsible for acid rain, and is a principle component of industrial smog. The current commercial technology for removing sulfur compounds from petroleum fuels is hydrodesulfurization (HDS). HDS uses hydrogen in the presence of a catalyst (typically Co—Mo supported on alumina) to convert thiols, sulfides, disulfides and benzothiophenes to sulfur-free hydrocarbons and hydrogen sulfide. Operating temperatures typically range from 260 to 400° C. and 3-5 MPa hydrogen pressure. The sulfur-free hydrocarbons are recombined with petroleum streams, while the hydrogen sulfide is converted to elemental sulfur in a Claus plant.

HDS is very effective at desulfurizing lighter petroleum streams such as gasoline and naphtha, but sulfur-removal from heavier streams such as kerosene and gas oil present a greater challenge. The reason for this is that heavier streams (boiling range>150° C.) contain sulfur in the form of benzothiophenes (bp 200-350° C.). Benzothiophenes (BT's) and their alkylated derivatives are more difficult to hydro-treat than the sulfides, disulfides and thiols contained in the lighter streams. Therefore higher temperatures and hydrogen pressures are required to remove BT's from heavier petroleum streams using HDS technology.

HDS technology will continue to be challenged in the future as environmental laws become more stringent and petroleum supplies become more heavy and sour. The problem facing the oil industry is that meeting current and future sulfur regulations also forces the industry to increase its green house gas ($CO_2$) emissions. This is based on the fact that using hydrogen gas to remove sulfur from oil is very energy intensive and leaves a large $CO_2$ emissions footprint. Therefore an alternative desulfurization technology is needed to either supplement or replace HDS. The most promising candidate is oxidative desulfurization (ODS). ODS technology uses an oxidant, often in the presence of a transition metal catalyst, to convert sulfides to sulfones under relatively mild conditions (50-90° C., atmospheric pressure). The sulfones are then removed from the petroleum stream by distillation, extraction, adsorption, etc. Therefore ODS serves to greatly reduce $CO_2$ emissions associated with the current HDS technology.

Most ODS attempts employed hydrogen peroxide (HP) as oxidant. Examples of catalytic systems that use HP are: $H_2O_2$-formic (or acetic) acid, titanium silicate, vanadium silicate, vanadium oxides supported on alumina, polyoxometalates, sodium tungstate and tungstophosphoric acid. However, HP is expensive and presents an economic barrier to ODS commercialization. An oxidant derived from air may be employed for ODS to be commercially viable.

Organohydroperoxides offer a good alternative to HP because they may be generated on site from air using existing petroleum streams, and their oxidation byproducts may be recombined with petroleum streams as oxygenates or sold in the fine chemicals market. To date, tert-butyl hydroperoxide (TBHP) has been the most frequently used alkyl hydroperoxide in ODS studies because it is a common industrial reagent. Examples of catalytic systems that have shown successful use of TBHP in ODS studies include: Re(V) oxo complex/$SiO_2$, $MoO_3/AlO_3$, and $WO_x/ZrO_2$. Cumyl hydroperoxide (CHP) has also been used in a study where ODS of model oil was performed in the presence of differing metal oxides (Fe, Co, Cu, V, Mo, Zr, Ti). Still other alkyl hydroperoxides used in ODS studies include cyclohexanone hydroperoxide (CY-HPO) and tert-amyl hydroperoxide (TAHP).

SUMMARY OF THE DISCLOSURE

A heterogeneous titanium(IV) catalyst has been developed, that is effective at selectively oxidizing benzothiophenes (BT's) under mild conditions of both model and real fuel streams using peroxides as oxidant. It has now been found that the catalyst of the present invention is useful in combination with organohydroperoxides. The pseudo-first order oxidation kinetics of dibenzothiophene (DBT) and 4,6-dimethyldibenzothiophene (DMDBT) in the presence of poly[bis(glycerolato)(hydroxo)(organoperoxo)titanium(IV) bisphenol A ester] using tert-butyl hydroperoxide (TBHP), cumyl hydroperoxide (CHP) and ethylbenzene hydroperoxide (EBHP) as oxidants are disclosed.

The present invention relates to a sulfoxidation method comprising providing a hydrocarbon stream including at least one sulfur compound; providing an oxidant comprising organohydroperoxide; providing a catalyst comprising a metal compound represented by the general formula $M(OOR)(OH)(OR')_2$; and contacting the hydrocarbon stream with the oxidant in the presence of the catalyst, resulting in the oxidation of at least one sulfur compound.

Other features, aspects, and advantages of the present invention will become better understood with reference to the following description.

DETAILS OF THE DISCLOSURE

Figure 1:
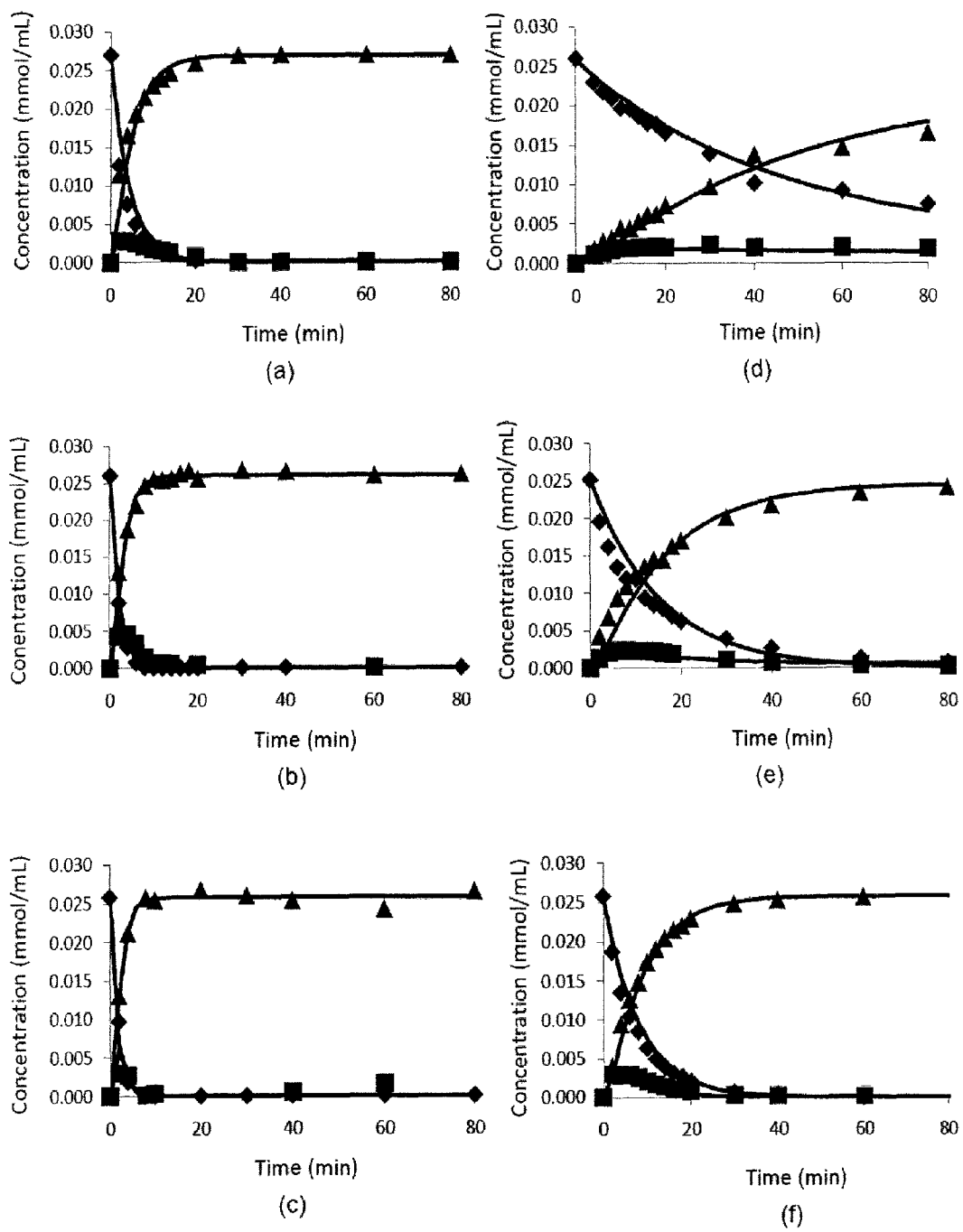
FIG. 1 (a-f) illustrates reaction profiles for the pseudo-first order oxidations of DBT and DMDBT at 85° C. up to 80 minutes; Sulfide (♦); Sulfoxide (■); Sulfone (▲). (a) DBT/TBHP, (b) DBT/CHP, (c) DBT/EBHP, (d) DMDBT/TBHP, (e) DMDBT/CHP, (f) DMDBT/EBHP.

While this disclosure contains many specific details, it should be understood that various changes and modifications may be made without departing from the scope of the technology herein described. The scope of the technology shall in no way be construed as being limited to the number of constituting components, the concentration of constituting components, the materials thereof, the shapes thereof, the relative arrangement thereof, the temperature employed, the order of combination of constituents thereof, etc., and are disclosed simply as examples. The depictions and schemes shown herein are intended for illustrative purposes and shall in no way be construed as being limiting in the number of constituting components, connectivity, reaction steps, the materials thereof, the shapes thereof, the relative arrangement thereof, the order of reaction steps thereof, etc., and are disclosed simply as an aid for understanding. The examples described herein relate to the removal of sulfur from hydrocarbon streams and they relate to catalysts suitable for use in the oxidative desulfurization of fluid streams of crude oil, diesel fuels, and cracked gasolines (e.g. thermally processed gasoline such as thermally cracked gasoline, visbreaker gasoline, coker gasoline and catalytically cracked gasoline). In addition, the examples described herein relate to methods for the removal of sulfur compounds from fluid streams of cracked gasoline and diesel fuels employing metal catalysts.

A sulfoxidation method comprising providing a hydrocarbon stream including at least one sulfur compound; providing an oxidant; providing a heterogeneous titanium(IV) catalyst; and contacting the hydrocarbon stream with the oxidant in the presence of the catalyst, resulting in the oxidation of at least one sulfur compound is disclosed. The sulfoxidation may generally be carried out at a pressure in the range of from about 0.5 atmospheres to about 10 atmospheres, particularly about atmospheric pressure, and at a temperature in the range from about 50° to about 90° C., with a reaction time in the range of from about 30 minutes to about 120 minutes.

The heterogeneous titanium(IV) catalyst comprises a metal compound, either polymeric or monomeric, represented by the general formula $M(OOR)(OH)(OR')_2$, wherein M is a metal, such as, for example, titanium or any metal, including, but not limited to, rhenium, tungsten or other transition metals alone or in combination that causes the chemical conversion of the sulfur species, as described herein. R is a group comprising hydride, alkyl groups (including linear, branched, saturated, unsaturated, cyclic and substituted alkyl groups, and wherein heteroatoms, such as oxygen, nitrogen, sulfur, silicon, phosphorus, and the like may be present in the alkyl group), typically from about 1 to about 22 carbon atoms, preferably from 1 to about 10 carbon atoms, although the number of carbon atoms may be outside these ranges, aryl groups (including substituted aryl), typically from about 6 to 30 carbon atoms, preferably from 6 to about 12 carbon atoms, although the number of carbon atoms may be outside these ranges, such as benzyl or the like, alkylaryl groups (including substituted alkylaryl groups), typically from about 7 to about 30 carbon atoms, preferably from about 7 to about 15 carbon atoms, although the number of carbon atoms may be outside of these ranges, and mixtures thereof wherein R' is a group comprising ethylene glycol, glycerol, sorbitol, xylitol and/or mixtures thereof, either un-polymerized or polymerized by reaction with a compound Q-R-Q' wherein Q and Q' each independently comprise an isocyanate, anhydride, sulfonyl halide, benzyl halide, carboxylic acid halide, phosphoryl acid halide, silyl chloride, or any chemical functionality capable of reacting with an —OH group of the polyol ligand, and wherein R comprises a linking group. The chain length of the polymeric catalyst may be between 1 and 1,000,000 repeat units, and the polymer chains may be cross-linked or un-crosslinked.

In one embodiment, the catalyst comprises a polymeric (hydroxo)bis(polyol)(hydroperoxo)titanium(IV) catalyst wherein the polyol is selected from the group comprising ethylene glycol, glycerol, sorbitol, xylitol and/or mixtures thereof.

In another embodiment, the catalyst comprises a polymeric (hydroxo)bis(polyol)(organoperoxo)titanium(IV) catalyst wherein the polyol is selected from the group comprising ethylene glycol, glycerol, sorbitol, xylitol and/or mixtures thereof, particularly the catalyst comprises poly[bis(glycerolato)(hydroxo)(organoperoxo)titanium(IV) bisphenol A ester]. The pendant —OH group of the polyol selectively detaches from the titanium center to allow a sulfide or sulfoxide to attach to the titanium center and thereby become oxidized. The —OH group of the polyol selectively blocks the oxidation of other species, such as olefins and benzylic hydrocarbons, by remaining attached to the titanium center.

The heterogeneous titanium(IV) catalyst may be prepared by the reaction of bis(glycerolato)oxotitanium(IV) with 4,4' bisphenol A dianhydride (as disclosed in Example 46 in International Publication WO2009/120238A1), incorporated herein by reference in its entirety, followed by reaction with hydroperoxide. An intermediate free complex of heterogeneous titanium(IV) catalyst may be formed with specific coordination of an organoperoxo group.

The hydroperoxide is of the general formula HOOR and R is a group comprising hydride, alkyl groups (including linear, branched, saturated, unsaturated, cyclic and substituted alkyl groups, and wherein heteroatoms, such as oxygen, nitrogen, sulfur, silicon, phosphorus, and the like may be present in the alkyl group), typically from about 1 to about 22 carbon atoms, preferably from 1 to about 10 carbon atoms, although the number of carbon atoms may be outside these ranges, aryl groups (including substituted aryl), typically from about 6 to 30 carbon atoms, preferably from 6 to about 12 carbon atoms, although the number of carbon atoms may be outside of these ranges, such as benzyl or the like, alkylaryl groups (including substituted alkylaryl groups), typically from about 7 to about 30 carbon atoms, preferably from about 7 to about 15 carbon atoms, although the number of carbon atoms may be outside of these ranges, and mixtures thereof.

The heterogeneous titanium(IV) catalyst may be in pellet or powder form, wherein the pellet may incorporate an inert organic or inorganic material as a binder, such as, but not limited to, aluminum oxide or polyvinylidene fluoride, or any substance that aids in the formation and strengthening of the catalyst pellet.

The heterogeneous titanium(IV) catalyst may be supported on an inorganic or organic support material including, but not limited to, oxides, inert or active, such as, for example, a porous support, such as talc or inorganic oxides.

Suitable inorganic oxides include, but are not limited to, oxides of elements of groups IB, II-A and II-B, III-A and II-B, IV-A and IV-B, V-A and V-B, VI-B, of the Periodic Table of the Elements. Examples of oxides preferred as supports include silicon dioxide, aluminum oxide, and/or mixed oxides of silicon and aluminum. Other suitable inorganic oxides which may be used alone or in combination with the abovementioned preferred oxide supports may be, for example, MgO, $ZrO_2$, $TiO_2$, CaO and/or mixtures thereof.

The support materials used may have a specific surface area in the range from 10 to 1000 $m^2/g$, a pore volume in the range from 0.1 to 5 ml/g and a mean particle size of from 0.1 to 10 cm. Preference may be given to supports having a specific surface area in the range from 0.5 to 500 $m^2/g$, a pore volume in the range from 0.5 to 3.5 ml/g and a mean particle size in the range from 0.5 to 3 cm. Particular preference may be given to supports having a specific surface area in the range from 200 to 400 $m^2/g$, and a pore volume in the range from 0.8 to 3.0 ml/g.

The organohydroperoxide oxidant is of the general formula HOOR, and R is a group consisting of alkyl groups (including linear, branched, saturated, unsaturated, cyclic and substituted alkyl groups, and wherein heteroatoms, such as oxygen, nitrogen, sulfur, silicon, phosphorus, and the like may be present in the alkyl group), typically from about 1 to about 22 carbon atoms, preferably from 1 to about 10 carbon atoms, although the number of carbon atoms may be outside these ranges, aryl groups (including substituted aryl), typically from about 6 to 30 carbon atoms, preferably from 6 to about 12 carbon atoms, although the number of carbon atoms may be outside of these ranges, such as benzyl or the like, alkylaryl groups (including substituted alkylaryl groups), typically from about 7 to about 30 carbon atoms, preferably from about 7 to about 15 carbon atoms, although the number of carbon atoms may be outside of these ranges, and mixtures thereof. Suitable organohydroperoxides include, but are not limited to, tert-butyl hydroperoxide (TBHP), cumyl hydroperoxide (CHP), ethylbenzene hydroperoxide (EBHP) and/or mixtures thereof.

The oxidant may also comprise an oxidized petroleum slip stream of naptha, diesel, or any other oxidized petroleum cut that may be oxidized to organohydroperoxides. Further, sulfoxidation rates may be optimized based on choice of organohydroperoxide as oxidant.

EXAMPLES

The following examples describe the preparation of poly [bis(glycerolato)(hydroxo)(organoperoxo)titanium(IV) bisphenol A ester] catalysts of the present invention. The experiments also test the kinetic behavior of poly[bis(glycerolato)(hydroxo)(organoperoxo)titanium(IV) bisphenol A ester] catalysts of the present invention in the sulfoxidation of DBT and DMDBT using TBHP, CHP and EBHP as oxidants, as well as test the non-reactivity of the heterogeneous titanium(IV) catalyst towards certain olefins and benzylic hydrocarbons, and, in addition, those experiments used to test catalyst leaching and recycle under reaction conditions. Also included is an example where a straight-run diesel sample is desulfurized using the poly[bis(glycerolato)(hydroxo) (cumylperoxo)titanium(IV) bisphenol A ester] of the present invention as sulfoxidation catalyst and CHP as oxidant.

Example 1

Heterogeneous poly[bis(glycerolato)(hydroxo)(ethylbenzylperoxo)titanium (IV) bisphenol A ester] Catalyst Preparation Heterogeneous poly[bis(glycerolato)(hydroxo)(ethylbenzylperoxo)titanium (IV) bisphenol A ester] catalyst is prepared by contacting a white poly[bis(glycerolato)oxotitanium(IV) bisphenol A ester] with about 50 wt % hydrogen peroxide solution in glacial acetic acid at about 23° C. to give the orange poly[bis (glycerolato)(hydroxo)(hydroperoxo)titanium(IV) bisphenol A ester]. The color change is an indication that poly[bis (glycerolato)oxotitanium(IV) bisphenol A ester] complex is peroxidated to poly[bis(glycerolato)(hydroxo)(hydroperoxo)titanium(IV) bisphenol A ester]. Poly[bis(glycerolato) (hydroxo)(hydroperoxo)titanium(IV) bisphenol A ester] is washed with glacial acetic acid and dried in the air. Poly[bis (glycerolato)(hydroxo)(hydroperoxo)titanium(IV) bisphenol A ester] is then contacted with toluene at about 85° C. for about 30 minutes and dried in air. This step is used to destroy any residual hydrogen peroxide and peroxyacetic acid that may be present in the catalyst. The catalyst is then contacted with a solution of ethylbenzene hydroperoxide in ethylbenzene (about 11 wt %) at about 35° C. from about 20 min to about 60 minutes in air. The catalyst is then filtered, washed with toluene and dried in air, to give the yellow to orange poly[bis(glycerolato)(hydroxo)(ethylbenzylperoxo)titanium (IV) bisphenol A ester]. Additional details of the preceding preparation are contained in international publication number WO 2009/120238 A1, published Oct. 1, 2009, the disclosure of which is hereby incorporated by reference to the extent not inconsistent with the present disclosure.

Example 2

Heterogeneous poly[bis(glycerolato)(hydroxo)(cumylperoxo)titanium(IV) bisphenol A ester] Catalyst Preparation Heterogeneous poly[bis(glycerolato)(hydroxo)(cumylperoxo)titanium(IV) bisphenol A ester] catalyst is prepared by contacting a white poly[bis(glycerolato)oxotitanium(IV) bisphenol A ester] with about 50 wt % hydrogen peroxide solution in glacial acetic acid at about 23° C. to give the orange poly[bis(glycerolato)(hydroxo)(hydroperoxo)titanium(IV) bisphenol A ester]. The color change is an indication that poly[bis(glycerolato)oxotitanium(IV) bisphenol A ester] complex is peroxidated to poly[bis(glycerolato)(hydroxo)(hydroperoxo)titanium(IV) bisphenol A ester]. Poly [bis(glycerolato)(hydroxo)(hydroperoxo)titanium(IV) bisphenol A ester] is washed with glacial acetic acid and dried in the air. Poly[bis(glycerolato)(hydroxo)(hydroperoxo)titanium(IV) bisphenol A ester] is then contacted with toluene at about 85° C. for about 30 minutes and dried in air. This step is used to destroy any residual hydrogen peroxide and peroxyacetic acid that may be present in the catalyst. The catalyst is then contacted with cumyl hydroperoxide (about 88 wt %) at about 35° C. from about 20 min to about 60 minutes in air. The catalyst is then filtered, washed with toluene and dried in air, to give the yellow to orange poly[bis(glycerolato)(hydroxo) (cumylperoxo)titanium(IV) bisphenol A ester]. Additional details of the preceding preparation are contained in international publication number WO 2009/120238 A1, published Oct. 1, 2009, the disclosure of which is hereby incorporated by reference to the extent not inconsistent with the present disclosure.

Example 3

Heterogeneous poly[bis(glycerolato)(hydroxo)(t-butylperoxo)titanium(IV) bisphenol A ester] Catalyst Preparation Heterogeneous poly[bis(glycerolato)(hydroxo)(t-butylperoxo)titanium(IV) bisphenol A ester] catalyst is prepared by contacting a white poly[bis(glycerolato)oxotitanium(IV) bisphenol A ester] with about 50 wt % hydrogen peroxide solution in glacial acetic acid at about 23° C. to give the orange poly[bis(glycerolato)(hydroxo)(hydroperoxo)titanium(IV) bisphenol A ester]. The color change is an indication that poly[bis(glycerolato)oxotitanium(IV) bisphenol A ester] complex is peroxidated to poly[bis(glycerolato)(hydroxo)(hydroperoxo)titanium(IV) bisphenol A ester]. Poly[bis(glycerolato)(hydroxo)(hydroperoxo)titanium(IV) bisphenol A ester] is washed with glacial acetic acid and dried in the air. Poly[bis(glycerolato)(hydroxo)(hydroperoxo)titanium(IV) bisphenol A ester] is then contacted with toluene at about 85° C. for about 30 minutes and dried in air. This step is used to destroy any residual hydrogen peroxide and peroxyacetic acid that may be present in the catalyst. The catalyst is then contacted with a solution of tert-butyl hydroperoxide (about 70 wt %) at about 35° C. from about 20 min to about 60 minutes in air. The catalyst is then filtered, washed with toluene and dried in air, to give the yellow to orange poly[bis(glycerolato)(hydroxo)(tert-butylperoxo)titanium(IV) bisphenol A ester]. Additional details of the preceding preparation are contained in international publication number WO 2009/120238 A1, published Oct. 1, 2009, the disclosure of which is hereby incorporated by reference to the extent not inconsistent with the present disclosure.

Example 4

Pseudo-First Order Kinetics Experiment

Model oil is prepared in a glass batch reactor by dissolving dibenzothiophene (about 73 mg, about 0.4 mmol) in cumene (about 13 g). Cumyl hydroperoxide (about 88 wt %, about 0.7 g, about 4 mmol) is added to the solution and is immediately followed by the catalyst prepared in accordance with Example 2 (about 5 g, about 8 mmol Ti(IV)). The reaction is allowed to proceed with stirring at about 85° C. in air. Aliquots (about 1 mL each) of the reaction mixture are removed about every 2 minutes up to about 20 minutes, and then about 10 to about 20 minutes up to about 80 minutes. Samples are passed through a syringe filter (0.25 mm, 0.22 micron) to remove catalyst and then diluted to the desired concentration with tetrahydrofuran. These samples are then analyzed by HPLC in order that the dibenzothiophene (DBT), dibenzothiophene sulfoxide (DBTSO) and dibenzothiophene sulfone ($DBTSO_2$) that are present in the sample might be quantified. After quantifying these compounds a reaction profile is constructed. The reaction profile (shown in FIG. 1(b)) enables the calculation of sulfoxidation reaction rates.

Example 5

Pseudo-First Order Kinetics Experiment

Model oil is prepared in a glass batch reactor by dissolving dibenzothiophene (about 72 mg, about 0.4 mmol) in ethylbenzene (about 9 g). A solution of ethylbenzene hydroperoxide in ethylbenzene (about 11 wt %, about 4.7 g, about 3.7 mmol) is added to the solution and is immediately followed by the catalyst prepared in accordance with Example 1 (about 5.0 g, about 8 mmol Ti(IV)). The reaction is allowed to proceed with stiffing at about 85° C. in air. Aliquots (about 1 mL each) of the reaction mixture are removed about every 2 minutes up to about 20 minutes, and then about 10 minutes up to about 80 minutes. Samples are passed through a syringe filter (0.25 mm, 0.22 micron) to remove catalyst and then diluted to the desired concentration with tetrahydrofuran. These samples are then analyzed by HPLC in order that the dibenzothiophene (DBT), dibenzothiophene sulfoxide (DBTSO) and dibenzothiophene sulfone ($DBTSO_2$) that are present in the sample might be quantified. After quantifying these compounds a reaction profile is constructed. The reaction profile (shown in FIG. 1(c)) enables the calculation of sulfoxidation reaction rates.

Example 6

Pseudo-First Order Kinetics Experiment

Model oil is prepared in a glass batch reactor by dissolving dibenzothiophene (about 73 mg, about 0.4 mmol) in tetralin (about 15 g). Tert-butyl hydroperoxide (about 70 wt %, about 0.49 g, about 3.8 mmol) is added to the solution and is immediately followed by the catalyst prepared in accordance with Example 3 (about 5.0 g, about 8.4 mmol Ti(IV)). The reaction is allowed to proceed with stirring at about 85° C. in air. Aliquots (about 1 mL each) of the reaction mixture are removed about every 2 minutes up to about 20 minutes, and then about 10 to about 20 minutes up to about 80 minutes. Samples are passed through a syringe filter (0.25 mm, 0.22 micron) to remove catalyst and then diluted to the desired concentration with tetrahydrofuran. These samples are then analyzed by HPLC in order that the dibenzothiophene (DBT), dibenzothiophene sulfoxide (DBTSO) and dibenzothiophene sulfone ($DBTSO_2$) that are present in the sample might be quantified. After quantifying these compounds a reaction profile is constructed. The reaction profile (shown in FIG. 1(a)) enables the calculation of sulfoxidation reaction rates.

Example 7

Pseudo-First Order Kinetics Experiment

Model oil is prepared in a glass batch reactor by dissolving dimethyldibenzothiophene (about 82 mg, about 0.4 mmol) in cumene (about 13 g). Cumyl hydroperoxide (about 88 wt %, about 0.68 g, about 3.9 mmol) is added to the solution and is immediately followed by the catalyst prepared in accordance with Example 2 (about 5.0 g, about 8.4 mmol Ti(IV)). The reaction is allowed to proceed with stirring at about 85° C. in air. Aliquots (about 1 mL each) of the reaction mixture are removed about every 2 minutes up to about 20 minutes, and then about 10 to about 20 minutes up to about 80 minutes. Samples are passed through a syringe filter (0.25 mm, 0.22 micron) to remove catalyst and then diluted to the desired concentration with tetrahydrofuran. These samples are then analyzed by HPLC in order that the dimethydibenzothiophene (DBT), dimethyldibenzothiophene sulfoxide (DBTSO) and dimethyldibenzothiophene sulfone ($DBTSO_2$) that are present in the sample might be quantified. After quantifying these compounds a reaction profile is constructed. The reaction profile (shown in FIG. 1(e)) enables the calculation of sulfoxidation reaction rates.

Example 8

Pseudo-First Order Kinetics Experiment

Model oil is prepared in a glass batch reactor by dissolving dimethyldibenzothiophene (about 83 mg, about 0.4 mmol) in ethylbenzene (about 8.8 g). A solution of ethylbenzene hydroperoxide in ethylbenzene (about 11 wt %, about 4.8 g, about 3.8 mmol) is added to the solution and is immediately followed by the catalyst prepared in accordance with Example 1 (about 5.0 g, about 8.4 mmol Ti(IV)). The reaction is allowed to proceed with stiffing at about 85° C. in air. Aliquots (about 1 mL each) of the reaction mixture are removed about every 2 minutes up to about 20 minutes, and then about 10 to about 20 minutes up to about 80 minutes. Samples are passed through a syringe filter (0.25 mm, 0.22 micron) to remove catalyst and then diluted to the desired concentration with tetrahydrofuran. These samples are then analyzed by HPLC in order that the dimethydibenzothiophene (DBT), dimethyldibenzothiophene sulfoxide (DBTSO) and dimethyldibenzothiophene sulfone (DBTSO$_2$) that are present in the sample might be quantified. After quantifying these compounds a reaction profile is constructed. The reaction profile (shown in FIG. 1(f)) enables the calculation of sulfoxidation reaction rates.

Example 9

Pseudo-First Order Kinetics Experiment

Model oil is prepared in a glass batch reactor by dissolving dimethyldibenzothiophene (about 83 mg, about 0.4 mmol) in tetralin (about 15 g). Tert-butyl hydroperoxide (about 88 wt %, about 0.68 g, about 3.9 mmol) is added to the solution and is immediately followed by the catalyst prepared in accordance with Example 3 (about 5.0 g, about 8.4 mmol Ti(IV)). The reaction is allowed to proceed with stiffing at about 85° C. in air. Aliquots (about 1 mL each) of the reaction mixture are removed about every 2 minutes up to about 20 minutes, and then about 10 to about 20 minutes up to about 80 minutes. Samples are passed through a syringe filter (0.25 mm, 0.22 micron) to remove catalyst and then diluted to the desired concentration with tetrahydrofuran. These samples are then analyzed by HPLC in order that the dimethydibenzothiophene (DBT), dimethyldibenzothiophene sulfoxide (DBTSO) and dimethyldibenzothiophene sulfone (DBTSO$_2$) that are present in the sample might be quantified. After quantifying these compounds a reaction profile is constructed. The reaction profile (shown in FIG. 1(d)) enables the calculation of sulfoxidation reaction rates.

Example 10

Pseudo-First Order Kinetics Experiment

A diesel slip stream is oxidized between 50 and 150° C. and in the presence of base and between 1 and 200 atmospheres of air pressure.

Model oil is prepared in a glass batch reactor by dissolving dimethyldibenzothiophene (about 83 mg, about 0.4 mmol) in the oxidized diesel stream (15 g). The catalyst prepared in accordance with Example 1 (about 5.0 g, about 8.4 mmol Ti(IV)) is then immediately added. The reaction is allowed to proceed with stirring at about 85° C. in air. Aliquots (about 1 mL each) of the reaction mixture are removed about every 2 minutes up to about 20 minutes, and then about 10 to about 20 minutes up to about 80 minutes. Samples are passed through a syringe filter (0.25 mm, 0.22 micron) to remove catalyst and then diluted to the desired concentration with tetrahydrofuran. These samples are then analyzed by HPLC in order that the dimethydibenzothiophene (DBT), dimethyldibenzothiophene sulfoxide (DBTSO) and dimethyldibenzothiophene sulfone (DBTSO$_2$) that are present in the sample might be quantified. After quantifying these compounds a reaction profile is constructed.

The samples in Examples 4-10, as set forth supra, are analyzed by HPLC on an HP Series II 1090 liquid chromatograph [diode-array detector detecting at 325 and 254 nm; Phenomenex Luna 5 μC18(2) 100A column (250×4.60 mm)] operating in gradient elution mode: 50:50 acetonitrile:water to 100% acetonitrile at about 20 minutes; column temperature: about 40° C. Concentrations of DBT and DMDBT (sulfides), as well as DBTSO$_2$ and DMDBTSO$_2$ (sulfones), in the samples are determined by calibration curves that are prepared from the pure compound. Concentrations of DBTSO and DMDBTSO in the samples are determined by an indirect method using the concentrations of the sulfide and sulfone. These values are arrived at by subtracting the concentrations of sulfone and sulfide at time t from the beginning sulfide concentration (time=0). The presence of the sulfoxides and sulfones are further confirmed by GC-MS using an HP 5890 Series II gas chromatograph [HP 5970 mass spectrometer detector; column: Zebron ZB-1 Inferno, 30 m×0.25 mm (ID)×0.25 μm (film thickness)] operating in a temperature-programmed mode: holding at about 150° C. for about 7 minutes and then ramping to about 250° C. at a rate of about 20° C./min, and then holding at temperature for about 15 minutes. Rate constants are calculated using Tenua, a kinetics program available at www.bililite.com, the disclosure of which is hereby incorporated by reference to the extent not inconsistent with the present disclosure.

Example 11

Olefin Reactivity

Model oil is prepared by dissolving styrene (about 0.26 g, about 2.5 mmol) in a solution of ethylbenzene hydroperoxide (EBHP) in ethylbenzene (about 11 wt %, about 3.4 g, about 2.7 mmol EBHP, about 1 mole equivalent relative to styrene). The catalyst prepared in accordance with Example 1 (about 1.3 g, about 2.1 mmol Ti(IV)) is added to the model oil and the reaction is heated with stiffing to about 85° C. in a glass-lined aluminum block reactor. The experiment is run for about 80 minutes. NMR samples are prepared in DMSO-d$_6$. Extent of reaction is monitored by $^1$H and $^{13}$C NMR spectroscopy. No oxidation of styrene is observed.

Example 12

Olefin Reactivity

Model oil is prepared by dissolving 1-hexene (about 0.22 g, about 2.6 mmol) in a solution of ethylbenzene hydroperoxide (EBHP) in ethylbenzene (about 11 wt %, about 3.4 g, about 2.7 mmol EBHP, about 1 mole equivalent relative to 1-hexene). The catalyst prepared in accordance with Example 1 (about 1.3 g, about 2.1 mmol Ti(IV)) is added to the model oil and the reaction is heated with stiffing to about 85° C. in a glass-lined aluminum block reactor. The experiment is run for about 80 minutes. NMR samples are prepared in DMSO-d$_6$. Extent of reaction is monitored by $^1$H and $^{13}$C NMR spectroscopy. No oxidation of 1-hexene is observed.

Example 13

Olefin Reactivity

Model oil is prepared by dissolving cyclohexene (about 0.20 g, about 2.6 mmol) in a solution of ethylbenzene hydroperoxide (EBHP) in ethylbenzene (about 11 wt %, about 3.4 g, about 2.7 mmol EBHP, about 1 mole equivalent relative to cyclohexene). The catalyst prepared in accordance with Example 1 (about 1.3 g, about 2.1 mmol Ti(IV)) is added to the model oil and the reaction is heated with stirring to about 85° C. in a glass-lined aluminum block reactor. The experiment is run for about 80 minutes. NMR samples are prepared in DMSO-$d_6$. Extent of reaction is monitored by $^1$H and $^{13}$C NMR spectroscopy. No oxidation of cyclohexene is observed.

Example 14

Olefin Reactivity

Model oil is prepared by dissolving limonene (about 0.35 g, about 2.6 mmol) in a solution of ethylbenzene hydroperoxide (EBHP) in ethylbenzene (about 11 wt %, about 3.4 g, about 2.7 mmol EBHP, about 1 mole equivalent relative to limonene). The catalyst prepared in accordance with Example 1 (about 1.3 g, about 2.1 mmol Ti(IV)) is added to the model oil and the reaction is heated with stiffing to about 85° C. in a glass-lined aluminum block reactor. The experiment is run for about 80 minutes. NMR samples are prepared in DMSO-$d_6$. Extent of reaction is monitored by $^1$H and $^{13}$C NMR spectroscopy. No oxidation of limonene is observed.

Example 15

Olefin Reactivity

Model oil is prepared by dissolving trans-stilbene (about 0.46 g, about 2.6 mmol) in a solution of ethylbenzene hydroperoxide (EBHP) in ethylbenzene (about 11 wt %, about 3.4 g, about 2.7 mmol EBHP, about 1 mole equivalent relative to trans-stilbene). The catalyst prepared in accordance with Example 1 (about 1.3 g, about 2.1 mmol Ti(IV)) is added to the model oil and the reaction is heated with stiffing to about 85° C. in a glass-lined aluminum block reactor. The experiment is run for about 80 minutes. NMR samples are prepared in DMSO-$d_6$. Extent of reaction is monitored by $^1$H and $^{13}$C NMR spectroscopy. No oxidation of trans-stilbene is observed.

Example 16

Benzylic Hydrocarbon Reactivity

Model oil is prepared by adding tetralin (about 0.35 g, about 2.6 mmol) to a solution of ethylbenzene hydroperoxide (EBHP) in ethylbenzene (about 11 wt %, about 3.4 g, about 2.7 mmol EBHP, about 1 mole equivalent relative to tetralin). The catalyst prepared in accordance with Example 1 (about 1.3 g, about 2.1 mmol Ti(IV)) is added to the model oil and the reaction is heated with stirring to about 85° C. in a glass-lined aluminum block reactor. The experiment is run for about 80 minutes. NMR samples are prepared in DMSO-$d_6$. Extent of reaction is monitored by $^1$H and $^{13}$C NMR spectroscopy. No oxidation of tetralin is observed.

Example 17

Benzylic Hydrocarbon Reactivity

Model oil is prepared by adding cumene (about 0.33 g, about 2.8 mmol) to a solution of ethylbenzene hydroperoxide (EBHP) in ethylbenzene (about 11 wt %, about 3.4 g, about 2.7 mmol EBHP, about 1 mole equivalent relative to cumene). The catalyst prepared in accordance with Example 1 (about 1.3 g, about 2.1 mmol Ti(IV)) is added to the model oil and the reaction is heated with stirring to about 85° C. in a glass-lined aluminum block reactor. The experiment is run for about 80 minutes. NMR samples are prepared in DMSO-$d_6$. Extent of reaction is monitored by $^1$H and $^{13}$C NMR spectroscopy. No oxidation of cumene is observed.

FIG. 1 shows the reaction profiles for the pseudo-first order oxidation of DBT and 4,6-DMDBT at 85° C. using the catalyst of the present invention. FIG. 1(a)-(c) correspond to the oxidation of DBT using TBHP, CHP and EBHP respectively. Similarly, FIGS. 1(d)-(f) represent the oxidation of DMDBT in the presence of TBHP, CHP and EBHP. All reactions follow an A-B-C mechanism, where sulfide is converted to sulfoxide and then sulfone.

It may be determined from FIG. 1 that reactivity is dependent upon both the oxidant identity and the substrate (DBT vs. DMDBT). When TBHP is used, DBT is completely oxidized to sulfone within about 25 minutes (FIG. 1(a)), however, by about 80 minutes DMDBT is only about 70% converted to about a 9:1 mixture of sulfone and sulfoxide, respectively (FIG. 1(d)). The DMDBT does not further react. CHP offers better results for both substrates: DBT is completely converted to sulfone by about 20 minutes (FIG. 1(b)) and DMDBT is completely converted to about 97% sulfone within about 80 minutes (FIG. 1(e)). EBHP gave the best oxidant performance. In its presence, DBT is completely oxidized to sulfone within about 10 minutes (FIG. 1(c)). Similarly, DMDBT is completely converted to sulfone by about 40 minutes (FIG. 1(f)).

The kinetic data in FIG. 1 is modeled using the A-B-C mechanism. Rate constants $k_1$ and $k_2$ are obtained for each reaction. Table 1 below shows the variation in $k_1$ (sulfide oxidation) and $k_2$ (sulfoxide oxidation) with substrate and oxidant.

Table 1 shows that for a given oxidant (compare entries 1 and 4, 2 and 5, and 3 and 6), $k_1$ of the DBT system is greater than that of the DMDBT system, giving the order of reactivity DBT>DMDBT. A similar trend is observed for $k_2$, where the order of reactivity is DBTSO>DMDBTSO. These results suggest that oxidation rates are controlled by steric, rather than electronic effects. The 4- and 6-methyl substitution on the phenyl rings of DMDBT hinder coordination to the metal, resulting in a slower oxidation rate than observed for DBT. A similar argument holds for sulfoxide oxidation.

TABLE 1

Pseudo-First Order Oxidation Kinetics of DBT and 4,6-DMDBT (all k are in sec$^{-1}$)

| Entry# | Substrate | Oxidant: | Mol Eq. Oxidant | $k_1$ (×10$^{-3}$) | $k_2$ (×10$^{-3}$) |
|---|---|---|---|---|---|
| 1 | DBT | TBHP | 9.5 | 6.87 | 16.5 |
| 2 | DBT | CHP | 9.5 | 10.3 | 17.0 |
| 3 | DBT | EBHP | 9.5 | 17.7 | 18.3 |
| 4 | DMDBT | TBHP | 9.5 | 0.37 | 3.67 |
| 5† | DMDBT | CHP | 9.5 | 0.75 | 8.33 |
| 6‡ | DMDBT | EBHP | 9.5 | 2.03 | 13.1 |

Conditions: 85° C., tetralin, ethylbenzene or cumene is used as model oil.
†$k_{-2}$ = 0.27 × 10$^{-3}$ sec$^{-1}$. This rate is artificial and arises from incomplete conversion of sulfoxide to sulfone due to oxidant decomposition over longer reaction times.
‡$k_{-1}$ = 0.37 × 10$^{-3}$ sec$^{-1}$; $k_{-2}$ = 0.20 × 10$^{-3}$ sec$^{-1}$. See explanation †.

Figure 2:
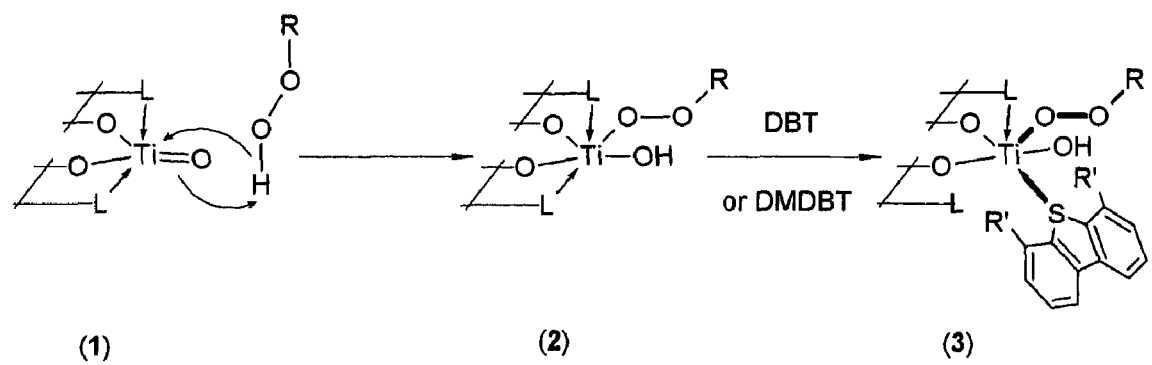
FIG. 2 illustrates proposed pathways for the peroxidation of titanium(IV) oxide with subsequent ligation of DBT or DMDBT.

Table 1 also shows that $k_1$ decreases as EBHP>CHP>TBHP (compare entries 1, 2 and 3, and 4, 5 and 6), when either DBT or DMDBT is the substrate. In order to better understand this trend, the conformational energy minima of DBT and DMDBT bound to a (hydroxo)($\eta^1$-organoperoxo)Ti(IV) intermediate (3) (FIG. 2) is modeled. The organoperoxo group shown in (3) comes from the reaction of a white Ti(IV) oxide (1) with organohydroperoxide to produce the yellow-orange complex (2). Subsequent coordination of DBT (or DMDBT) gives (3), the intermediate of interest. It is believed that (3) is the catalytically active species in sulfoxidation when using the catalyst as prepared in accordance with Examples 1-3. Similar intermediates have been proposed in the literature. The conformational modeling is performed by rotating the M-O, O—O, O—R and M←S bonds [bold bonds in (3)] while minimizing the structure using the MM2 molecular mechanics model. Calculations are performed for R'=H, $CH_3$ and R=$C_6H_5C(CH_3)_2$, $C_6H_5CH(CH_3)$ and $C(CH_3)_3$.

The conformational energy minimum is associated with the most favorable conformation of the organoperoxo group for substrate coordination. As this energy is raised due to steric constraints in the organoperoxo moiety, substrate coordination becomes less favorable and impedes the subsequent oxidation step. This leads to a decrease in $k_1$ and reduced oxidation rates.

Figure 3:
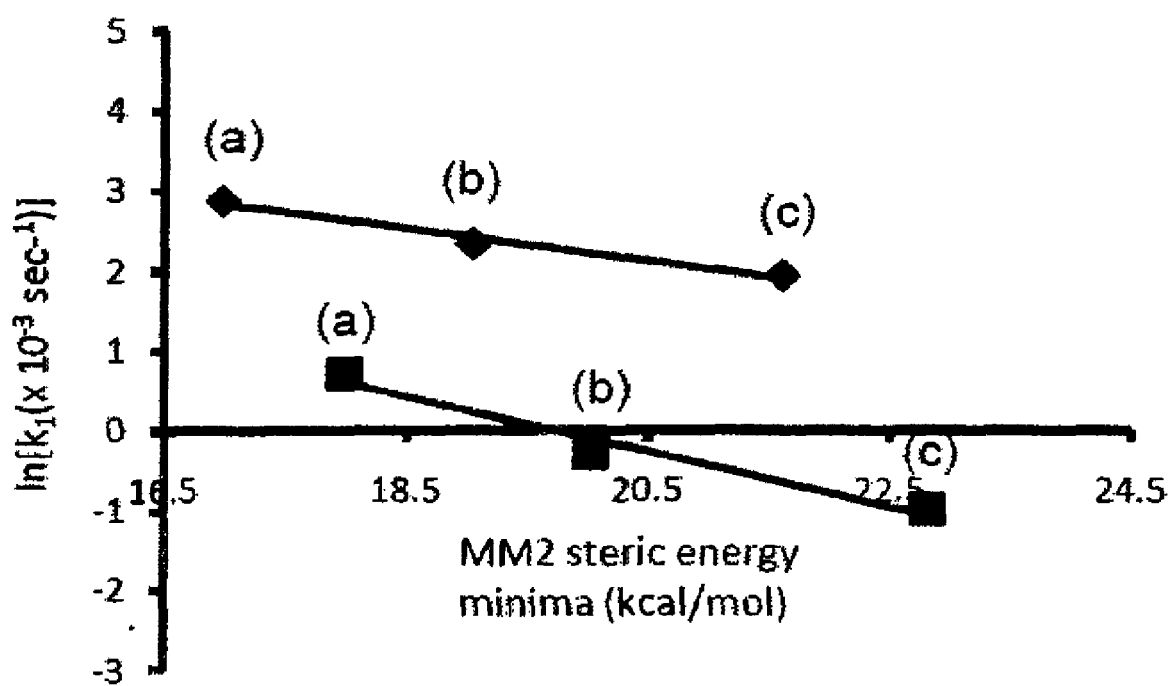
FIG. 3 illustrates In ($k_1$) for the oxidation of DBT(♦) and DMDBT (■) in the presence of EBHP, CHP and TBHP, plotted against the conformational energy minima of intermediate (3) where R=(a) $C_6H_5CH(CH_3)$, (b) $C_6H_5C(CH_3)_2$, and (c) $C(CH_3)_3$.

The conformational modeling indicated that $k_1$ shows a first order dependence upon the conformational energy minima of (3) (henceforth defined as the steric energy minima of (3)). FIG. 3 illustrates this effect by showing the plot of ln ($k_1$) for both the DBT and DMDBT catalytic systems versus the steric energy minima of (3) where R is varied. It is evident from the figure that ln ($k_1$) decreases linearly with an increase in the steric energy minima of (3). The steric energy minima are a measure of steric hindrance in the chemical system.

Steric energy minima increase in the following order as the organoperoxo group in (3) is varied: $C_6H_5CH(CH_3) < C_6H_5C(CH_3)_2 < C(CH_3)_3$. This data is in agreement with the observed oxidant order of reactivity EBHP>CHP>TBHP as shown in Table 1. As the steric energy minimum of intermediate (3) is increased, the substrate has more difficulty coordinating to the metal center because it is sterically hindered to some extent by the organoperoxo moiety. This reduces oxidation rates, and shows its effect through decreased $k_1$.

Figure 4:
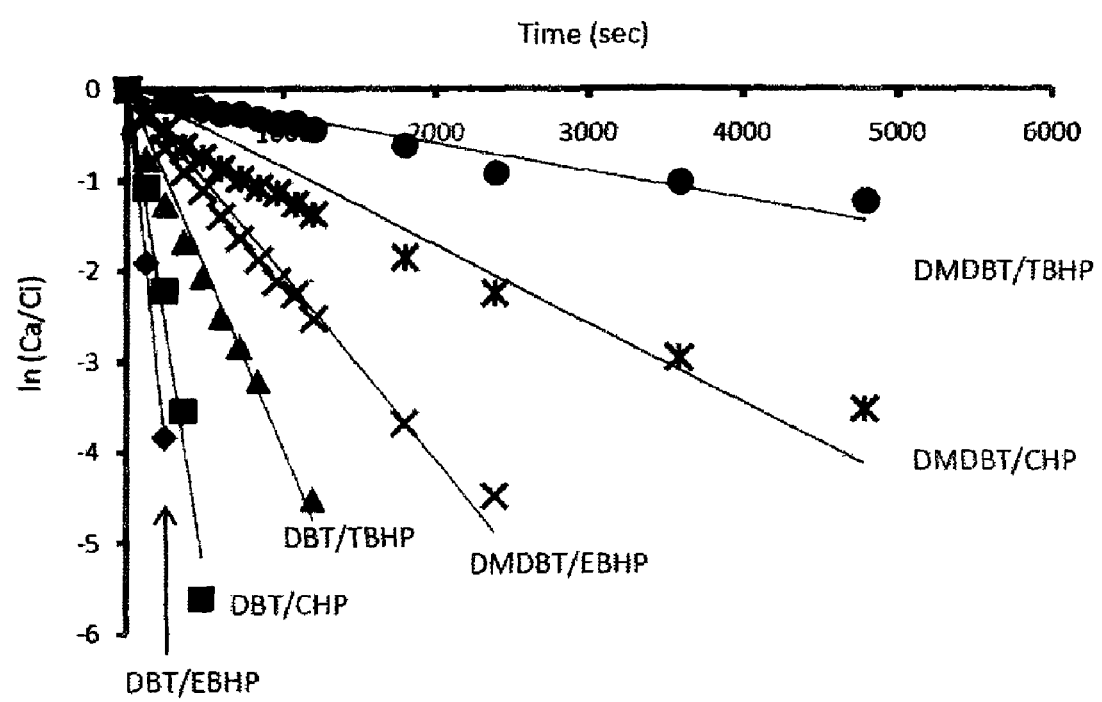
FIG. 4 illustrates the Pseudo-first order kinetics plot of DBT and DMDBT oxidation using EBHP, CHP and TBHP as oxidants.

FIG. 4 shows the first order rate plots for oxidation of DBT and DMDBT using EBHP, CHP and TBHP. This data is derived from the reaction profiles shown in FIG. 1. The slopes of the lines correspond to $k_1$ The rate constants $k_1$ ($sec^{-1}$) for each specific sulfide/organohydroperoxide couple are equal to: DBT/EBHP (0.016), DBT/CHP (0.010), DBT/TBHP (0.004), DMDBT/EBHP (0.002), DMDBT/CHP (0.0004) and DMDBT/TBHP (0.0003), and are in good agreement with the modeled rate data provided in Table 1.

FIG. 4 is an illustration of the steric factors influencing $k_1$. All of the reactions involving DBT are faster than those of DMDBT due to the steric constraints of DMDBT coordination. Further, there is a greater difference between $k_1$'s as the oxidant is varied in the DMDBT reactions, relative to the DBT reactions. This is evident in FIG. 4 from the broader difference of slopes with change of oxidant, relative to those of the DBT reactions. This indicates that DMDBT reactivity is more sensitive to change in oxidant than is DBT reactivity. This makes sense because DMDBT coordination should be more easily sterically hindered by the organoperoxo group due to the 4- and 6-methyl substitution. This trend may also be reflected in FIG. 3, where the slope for the DMDBT $k_1$'s is greater than that for the DBT $k_1$'s, indicating greater sensitivity of the former to changes in the steric energy minima of (3).

It may also be seen from Table 1 that, for the oxidation of DBTSO, $k_2$ shows little change with oxidant steric hindrance, in contrast to $k_1$. This result may be explained by the mechanism displayed in FIG. 5. After the DBT coordinates to the metal center (3), it inserts into the M-OH bond, forming (4). Further reaction with the organoperoxo group yields the release of ROH and the formation of DBTSO and Ti(IV) oxide. Since it is believed that DBTSO is in close proximity to the metal, it may immediately coordinate to form (5). The sulfoxide may be bound prior to the peroxidation of the metal, therefore $k_2$ may be nearly unaffected by the bulkiness of the oxidant. Intermediate (5) may then be hydrolyzed by the organohydroperoxide forming (6).

Figure 5:
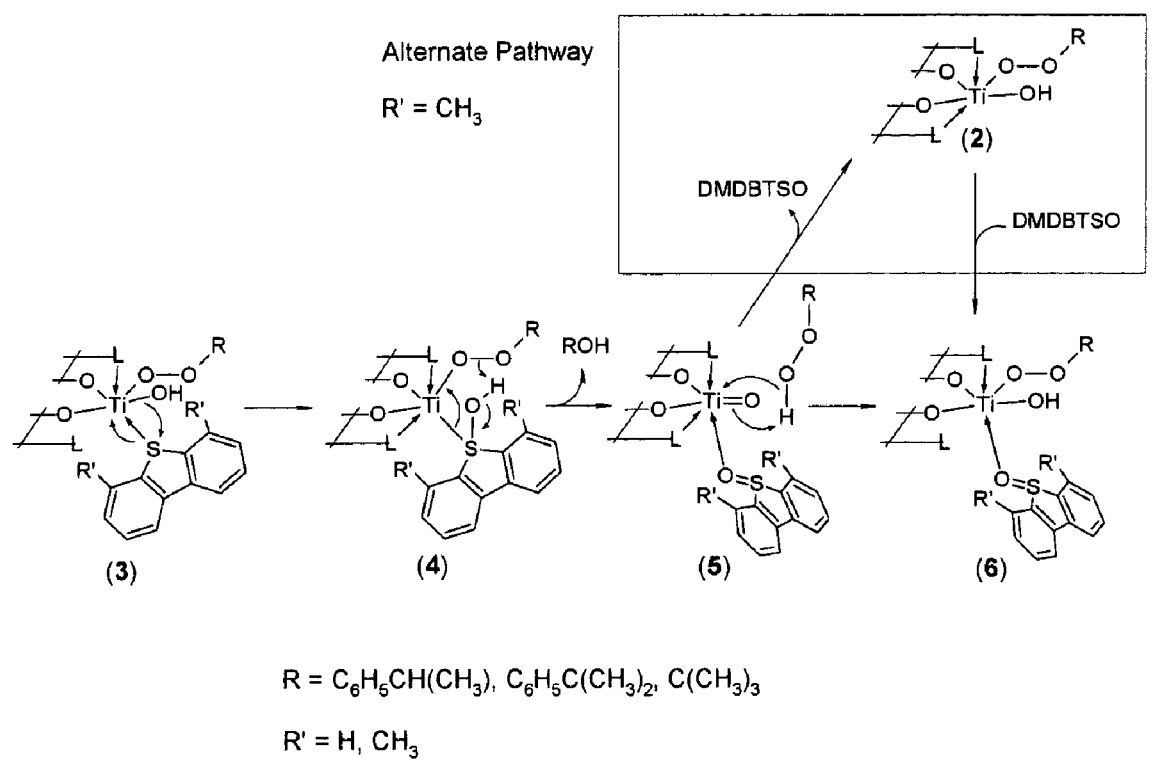
FIG. 5 illustrates a mechanism for the oxidation of DBT and DMDBT to sulfoxide.

In contrast to DBTSO, oxidation rates for DMDBTSO depend upon oxidant steric hindrance. In Table 1 it may be seen that $k_2$ (entries 4, 5 and 6) decreases as EBHP>CHP>TBHP, similar to that observed for $k_1$. This effect may be rationalized in the following way. DMDBT coordinates to the (hydroxo)($\eta^1$-organoperoxo)Ti(IV) intermediate to yield (3) (FIG. 5, R'=$CH_3$). DMDBT may be inserted into the metal-OH bond giving (4). Further reaction with the organohydroperoxide yields alcohol, and a Ti(IV) oxide with ligated DMDBTSO (5). In this case, the DMDBTSO may undergo a sterically-assisted dissociation from the metal center either just before or during the metal peroxidation step, yielding free DMDBTSO and complex (2) (FIG. 5, alternate pathway). The DMDBTSO may then coordinate to complex (2) to give (6). This coordination step may be controlled by the conformation of the organoperoxo group of (2) and therefore $k_2$ may show oxidant dependence.

Figure 6:
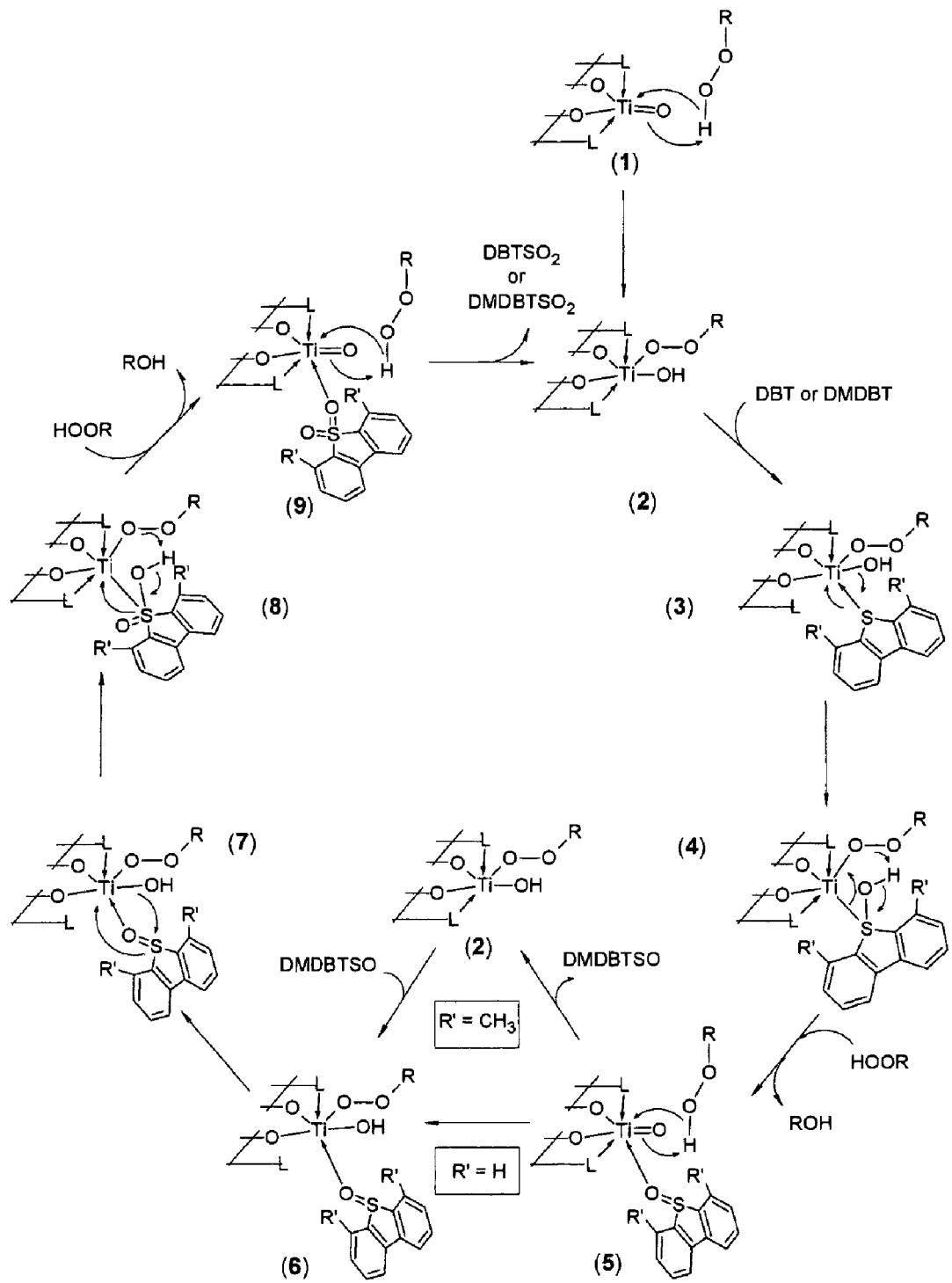
FIG. 6 illustrates a mechanism for DBT and DMDBT oxidation using the catalyst prepared in accordance with Example 1-3 and organohydroperoxide as oxidant.

FIG. 6 displays the proposed mechanism for the oxidation of DBT's using the catalyst prepared in accordance with Example 1, and variants thereof, as catalysts and organo hydroperoxides as oxidant. The spectator ligand's non-coordinating atoms, including those of the polyol and the polymer backbone, have been omitted for simplification purposes. First complex (1) may be peroxidated to coordinatively saturated complex (2). L (where L may be —OH) may dissociate and DBT (or DMDBT) may coordinate yielding intermediate (3). The organoperoxo group may be in a favorable conformation for coordination to occur in this step. DBT (or DMDBT) may then insert and L (where L may be —OH) may re-coordinate forming 6-coordinate (4). The $\eta^1$-organoperoxo ligand in (4) may abstract a proton from the S—OH moiety, generating ROH, sulfoxide and Ti(IV) oxide (5). In the case of DBTSO (R'=H), the sulfoxide may remain coordinated to the metal center through an oxygen lone pair. Intermediate (5) may then be peroxidated to (6) with concomitant dissociation of L (where L may be —OH). In contrast, DMDBTSO (R'=$CH_3$) may dissociate either immediately before, or during the peroxidation step to yield free sulfoxide and complex (2). When the $\eta^1$-organoperoxo group of (2) may be in the correct conformation, DMDBTSO may coordinate forming intermediate (6) with dissociation of L (where L may be —OH) The sulfoxide (DBTSO or DMDBTSO) then may undergo insertion into the metal-OH bond (7) and L (where L may be —OH) may re-coordinate, yielding intermediate (8). The $\eta^1$-organoperoxo group may abstract a proton from the S—OH moiety, forming ROH and a sulfone-coordinated Ti(IV) oxide (9). Peroxidation of (9) and dissociation of sulfone may form complex (2) and may complete the catalytic cycle.

One of the potential drawbacks of oxidative desulfurization of fuels has been the unselective oxidation of olefins and benzylic hydrocarbons to epoxides and alcohols, which occurs in addition to sulfoxidation with prior art catalysts. This poses a major difficulty for the commercialization of ODS, since oxidation of the fuel itself is undesirable. In order for an ODS catalyst to be fruitful, sulfur selective catalysts are required. The heterogeneous titanium(IV) catalyst of the present invention offers a solution to this problem, because under reaction conditions, no oxidation of olefins or benzylic hydrocarbons has been observed. For example, when a solution of about 1:1:1 olefin: EBHP: catalyst is heated to about 85° C. for about 80 minutes no epoxidation occurred. Olefins studied are styrene, 1-hexene, cyclohexene, limonene, and trans-stilbene. Furthermore, benzylic hydrocarbons tetralin and cumene are also un-oxidized to the corresponding alcohols under similar conditions.

One possible explanation for the S-selectivity of the catalyst prepared in accordance with Example 1 may be explained by the nature of complex (2). The organoperoxo ligand in complex (2) is $\eta^1$-coordinated and does not form an $\eta^2$-organoperoxo complex due to coordinate saturation. It is believed that $\eta^2$-organoperoxo complexes play a role in olefin epoxidation.

Figure 7:
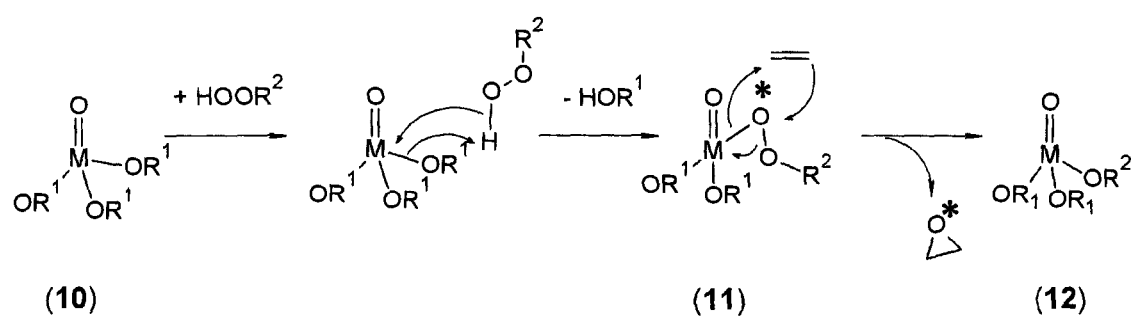
FIG. 7 illustrates an example of epoxidation via nucleophilic attack at the proximal oxygen of the organoperoxo ligand.

FIG. 7 shows an accepted mechanism for olefin epoxidation using an (alkoxy)M(oxide) as catalyst. In the mechanism, the (alkoxy)M(oxide) (10) may react with organohydroperoxide by losing an alkoxide ligand as alcohol and forming an (alkoxide)($\eta^2$-organoperoxo)M(oxide) (11). The organoperoxo ligand may coordinate if because of the coordinate unsaturation of complex (11). The $\eta^2$-coordination mode pins down the organo peroxo ligand, exposing the proximal oxygen (marked with * in FIG. 7). The olefin nucleophilically may attack the proximal oxygen of (11), yielding and epoxide and an (alkoxide)M(oxide) (12) that may be similar to the starting complex (10). If the organoperoxo ligand in (11) remained $\eta^1$-coordinant, the organoperoxo group would be free to rotate about the M-O, O—O and O—R bonds. This would make attack at the proximal oxygen much more difficult, and may greatly slow or inhibit olefin epoxidation. Thus the coordinate saturation of complex (2) may be a possible reason for the catalyst prepared in accordance with Example 1-3's S-selectivity; any potential substrate would have to be a better base than the chelating ligand L (where L may be —OH).

The catalyst of the present invention shows no signs of catalyst leaching under reaction conditions.

Example 18

Catalyst Recycle

Dibenzothiophene (about 0.30 g, about 1.6 mmol) is added to a glass batch reactor, followed by ethylbenzene (about 35 g). The catalyst prepared in accordance with Example 1 (about 20 g) is added to the resulting solution, followed by about 11 wt % EBHP in ethylbenzene (about 19 g, about 15 mmol EBHP, about 9.5 mole equivalents relative to DBT). The mixture is stirred at about 85° C. for about 80 minutes in a temperature-controlled water bath. Samples are removed from the mixture every 2 minutes up to 20 minutes, and then every 10 minutes up to 80 minutes. Samples are passed through a syringe filter (0.25 mm, 0.22 micron) to remove catalyst and then diluted to the desired concentration with tetrahydrofuran. Samples are assayed for DBT and $DBTSO_2$ by HPLC. A reaction profile is constructed and $k_1$ and $k_2$ are determined using the Tenua kinetics program. Catalyst is collected in a Buchner funnel, washed with toluene, and dried in the air. The procedure is then repeated re-using the catalyst. Rate constants $k_1$ and $k_2$ from the initial and recycle runs are compared to determine loss of catalyst activity. Rate constants $k_1$ are $14.2 \times 10^{-3}$ $sec^{-1}$ and $13.3 \times 10^{-3}$ $sec^{-1}$ for the initial and recycle runs, respectively. Rate constants $k_2$ also showed little difference between runs: $27.5 \times 10^{-3}$ $sec^{-1}$ and $27.2 \times 10^{-3}$ $sec^{-1}$ for the initial and recycle runs respectively. A decrease in rate constants should be observed if catalyst leaching occurred, however, rates remained nearly the same, suggesting that catalyst leaching does not occur to any great extent.

Example 19

Catalyst Leaching Study

Pelletized catalyst prepared in accordance with Example 1 (about 23 g, about 0.025 mol Ti(IV)) is added to a continuous loop reactor (reactor volume is about 35 mL). A 3:1 glacial acetic acid: tetralin solution (about 200 mL) is added to the reactor reservoir, and then the solvent is continuously passed over the catalyst (about 50° C., about 55 mL/min) for about 3 months. Samples (about 1 mL) of the solvent are removed on weekly intervals and replaced with fresh solvent (about 1 mL). Samples are submitted to Adirondack Environmental Services Inc. (Albany, N.Y.) for Ti elemental analysis. The elemental analysis data indicates that about 2 ppm titanium is present in the solvent after about 5 weeks up to about 3 months, at which time the experiment is completed. This indicates that little leaching of titanium(IV) occurred over this time. Thus even under harsher conditions, the catalyst prepared in accordance with Example 1 holds up quite well to leaching.

Example 20

Oxidative Desulfurization of Straight-Run Diesel

Figure 8:
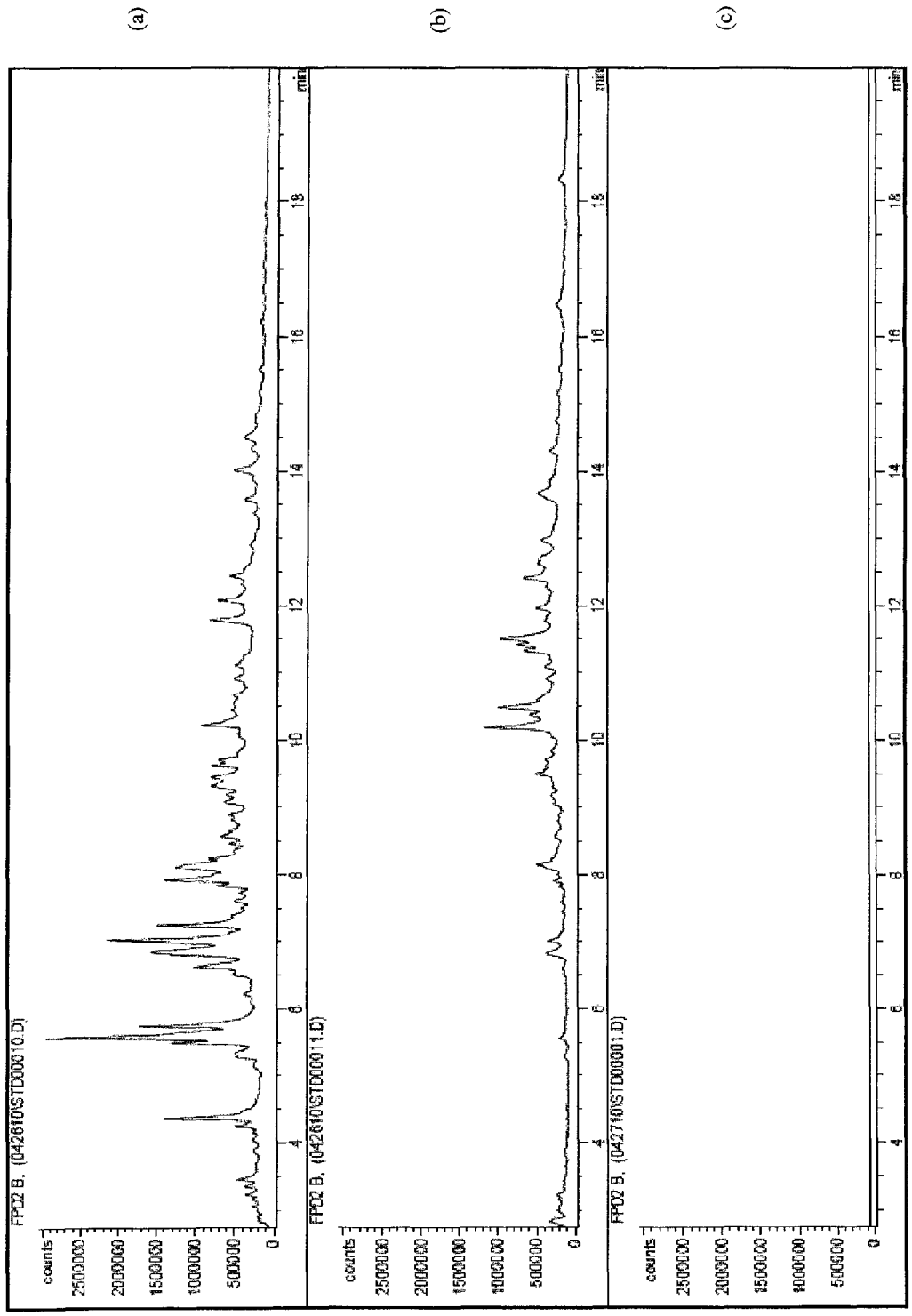
FIG. 8a illustrates a GC-SCD of a diesel (2327 ppm) prior to ODS treatment.
FIG. 8b illustrates peaks that correspond to aromatic sulfones such as $DBTSO_2$ from post-ODS diesel (2022 ppm), prior to the sulfone separation step.
FIG. 8c illustrates the absence of sulfone peaks in ODS diesel after sulfone separation (10.9 ppm S).

A straight-run diesel sample (about 3.6 g, about 1.8 wt % sulfur) is diluted with cumene (about 22 g). A portion of the modified diesel (about 21 g) is added to a glass batch reactor, followed by powdered catalyst prepare in accordance with Example 2 (about 7 g). A solution of about 88 wt % cumyl hydroperoxide (about 1.2 g, about 4 mole equivalents relative to sulfur) is added with stirring. The mixture is then heated to about 85° C. for about 80 minutes in a temperature-controlled water bath. At the end of the reaction the treated diesel is filtered free of catalyst and is assayed on an HP Series II gas chromatograph [column: Zebron ZB-1 HT; 30 m×0.25 mm (ID)×0.25 μm (film thickness); detector: sulfur-chemiluminescence detector (SCD)] operating in a temperature-programmed mode. The oven temperature is held at about 150° C. for about 5 minutes, ramped to about 200° C. (10° C./min) and held at temperature for about 25 minutes. FIG. 8(a) shows the GC-SCD chromatogram of real diesel prior to treatment. Peaks correspond to benzothiophene (BT) and DBT-like heteroaromatic impurities present in the diesel fuel. FIG. 8(b) shows the GC-SCD chromatogram of the diesel after treatment, but prior to any sulfone separation steps. The peaks show a characteristic shift to longer retention times that is indicative of sulfide to sulfone conversion.

Sulfones may be removed from the fuel stream by any combination of separation techniques, including distillation, extraction, and adsorption. FIG. 8(c) shows the GC-SCD chromatogram of post-separation treated diesel, where the diesel is reduced from 17500 ppm S to 10.9 ppm S. Thus, organohydroperoxide may be used with the catalyst prepared in accordance with Examples 1-3 in ODS to achieve ultra-low sulfur diesel (ULSD) sulfur levels.

The heterogeneous titanium(IV) catalyst has proven to be an effective heterogeneous catalyst for the oxidation of DBT's in both model and straight-run diesel using organohydroperoxide as oxidant. CHP, EBHP, and other potential organohydroperoxides may be used with the catalyst prepared in accordance with Examples 1-3 to produce ULSD levels via oxidative desulfurization. The use of organohydroperoxides in ODS is economically beneficial in contrast to HP because organohydroperoxides may be generated on-site from existing fuel streams, and their reaction byproducts, (aromatic-containing alcohols), may be used as fuel additives or marketed in the fine chemicals industry.

Further, the heterogeneous titanium(IV) catalyst of the present invention selectively oxidizes sulfides and shows little, if any signs of leaching under reaction conditions. Catalyst non-selectivity and leaching have presented obstacles to commercialization in prior art catalysts. It is believed that there are no commercial ODS processes in operation, primarily due to one or both of these factors.

The foregoing description of the embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the above described invention.

The invention claimed is:

1. A sulfoxidation method comprising:
providing a hydrocarbon stream comprising at least one sulfur compound;
providing an oxidant comprising organohydroperoxide;
providing a catalyst that selectively oxidizes sulfides, is substantially non-leaching, and is generated in situ, the catalyst comprising a metal compound represented by the general formula M(OOR)(OH)(OR')$_2$ wherein M is a metal; R is selected from the group consisting of hydride, alkyl groups, aryl groups, and/or alkylaryl groups; and wherein R' is selected from the group consisting of ethylene glycol, glycerol, sorbitol, xylitol and/or mixtures thereof
contacting the hydrocarbon stream with the oxidant in the presence of the catalyst, resulting in the oxidation of at least one sulfur compound.

2. The method of claim 1 wherein M is titanium.

3. The method of claim 1 wherein R' is polymerized by reaction with a compound Q-R-Q' wherein Q and Q' each independently is selected from the group consisting of isocyanate, anhydride, sulfonyl halide, benzyl halide, carboxylic acid halide, phosphoryl acid halide, silyl chloride and/or mixtures thereof and R is a linking group.

4. The method of claim 1 wherein the catalyst is prepared by the reaction of bis(glycerolato)oxotitanium(IV) with 4,4' bisphenol A dianhydride followed by reaction with hydroperoxide.

5. The method of claim 4 wherein the hydroperoxide is of the general formula HOOR wherein R is selected from the group consisting of hydride, alkyl groups, aryl groups, alkylaryl groups, and/or mixtures thereof.

6. The method of claim 5 wherein the catalyst comprises a polymeric (hydroxy)bis(polyol)(hydroperoxo)titanium(IV).

7. The method of claim 5 wherein the catalyst comprises a polymeric (hydroxy)bis(polyol)(organoperoxo)titanium (IV).

8. The method of claim 7 wherein the polyol is selected from the group consisting of ethylene glycol, glycerol, sorbitol, xylitol and/or mixtures thereof.

9. The method of claim 7 wherein a pendant —OH group of the polyol selectively detaches from a titanium center to allow a sulfide or sulfoxide to attach to the titanium center and thereby become oxidized, and wherein the pendant —OH group of the polyol selectively blocks the oxidation of non-sulfur containing compounds by remaining attached to the titanium center.

10. The method of claim 7 wherein an intermediate free complex of the catalyst is formed with specific coordination of an organoperoxo group.

11. The method of claim 1 wherein the organohydroperoxide is of the general formula HOOR, wherein R is selected from the group consisting of alkyl groups, aryl, alkylaryl groups and/or mixtures thereof.

12. The method of claim 11 wherein the organohydroperoxide is selected from the group consisting of ethylbenzene hydroperoxide, tert-butyl hydroperoxide, cumyl hydroperoxide and/or mixtures thereof.

13. The method of claim 1 wherein the method is carried out at a pressure in the range of from about 0.5 atmospheres to about 10 atmospheres and at a temperature in the range of from about 50° C. to about 90° C., with a reaction time in the range of from about 30 minutes to about 120 minutes.

14. The method of claim 1 wherein the catalyst is in pellet or powder form.

15. The method of claim 1 wherein the catalyst is supported on an inorganic or organic support material.

16. The method of claim 1 wherein the catalyst is poly[bis (glycerolato)(hydroxo)(ethylbenzylperoxo)titanium(IV) bisphenol A ester].

17. The method of claim 1 wherein the catalyst is poly[bis (glycerolato)(hydroxo)(cumylperoxo)titanium(IV) bisphenol A ester].

18. The method of claim 1 wherein the catalyst is poly[bis (glycerolato)(hydroxo)(tert-butylperoxo)titanium(IV) bisphenol A ester].

* * * * *